United States Patent [19]

Toja et al.

[11] Patent Number: 4,882,350

[45] Date of Patent: Nov. 21, 1989

[54] DERIVATIVES OF 1-BENZYL-2-OXO-5-ALKOXY-PYRROLIDINE, AND MEDICAMENT COMPOSITIONS CONTAINING THEM

[75] Inventors: Emilio Toja; Carlo Gorini, both of Milan; Fernando Barzaghi; Giulio Galliani, both of Monza, all of Italy

[73] Assignee: Roussel Uclaf, Paris, France

[21] Appl. No.: 211,288

[22] Filed: Jun. 24, 1988

[30] Foreign Application Priority Data

Jun. 25, 1987 [IT] Italy .................. 21046 A/87

[51] Int. Cl.$^4$ ............... A61K 31/40; C07D 207/27
[52] U.S. Cl. ............................. 514/425; 548/455
[58] Field of Search ................. 548/545; 514/425

[56] References Cited

U.S. PATENT DOCUMENTS

| | | | |
|---|---|---|---|
| 3,117,975 | 1/1964 | Bortnick et al. | 548/545 |
| 3,132,149 | 5/1964 | Bortnick et al. | 548/545 |
| 3,423,426 | 1/1969 | Kohn | 548/542 |
| 3,686,169 | 8/1972 | Coran et al. | 548/542 |
| 4,138,408 | 2/1979 | Mitzlaff | 548/545 |

FOREIGN PATENT DOCUMENTS

| | | | |
|---|---|---|---|
| 0138721 | 4/1985 | European Pat. Off. | |
| 2758939 | 8/1978 | Fed. Rep. of Germany | 548/544 |
| 0100051 | 8/1975 | Japan | 548/545 |

OTHER PUBLICATIONS

Drugs of the Future, vol. 10, No. 12, 1985, pp. 972, 974.

Primary Examiner—David B. Springer
Attorney, Agent, or Firm—Stevens, Davis, Miller & Mosher

[57] ABSTRACT

Compounds useful in the treatment of patients suffering from intellectual or nervous asthenias, memory failures, senescence or metal strain of the formula (I)

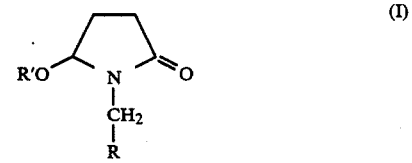

in which R' represents hydrogen, linear, branched or cyclic alkyl containing up to 12 carbon atoms, alkenyl containing from 2 to 8 carbon atoms, acyl containing from 1 to 6 carbon atoms or aralkyl containing from 7 to 15 carbon atoms and R represents aryl containing up to 14 carbon atoms, possibly substituted, or a mono- or polycyclic heterocyclic aromatic radical possibly substituted, provided that if R is unsubstituted phenyl, R' does not represent methyl or ethyl; also therapeutic compositions containing those compounds and method of use.

7 Claims, No Drawings

DERIVATIVES OF 1-BENZYL-2-OXO-5-ALKOXY-PYRROLIDINE, AND MEDICAMENT COMPOSITIONS CONTAINING THEM

This invention relates to new derivatives of 1-benzyl-2-oxo-5-alkoxy-pyrrolidine, the process for their preparation, their use as medicaments and the pharmaceutical compositions containing them.

The subject of the invention is the compounds (I):

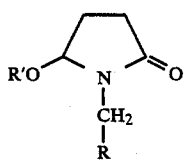

(I)

in which R' represents hydrogen, a linear, branched or cyclic alkyl containing up to 12 carbon atoms, alkenyl containing from 2 to 8 carbon atoms, acyl containing from 1 to 6 carbon atoms or aralkyl containing from 7 to 15 carbon atoms and R represents aryl containing up to 14 carbon atoms, possibly substituted, or a mono- or polycyclic heterocyclic aromatic radical, possibly substituted, provided that if R is unsubstituted phenyl, R' does not represent either methyl or ethyl.

As alkyl, there is preferred an alkyl containing from 3 to 10 carbon atoms, for example, n-propyl, isopropyl, n-butyl, isobutyl, tertbutyl, n-pentyl, n-hexyl, n-heptyl, n-octyl, cyclopropyl, cyclobutyl, cyclopentyl or cyclohexyl.

As alkenyl, there is preferred ethenyl, propenyl or butenyl.

As acyl, there is preferred acetyl, propionyl or butyryl.

As aralkyl, there is preferred phenalkyl, and particularly phenalkyl having 7 to 15 carbon atoms, e.g., benzyl or phenethyl.

As aryl, there is preferred phenyl or biphenylyl.

As heterocyclic radical, there is preferred a furyl, thienyl, pyranyl, pyridyl, benzofuranyl, isobenzofuranyl, chromanyl, isochromanyl, chromenyl, xanthenyl, phenoxathienyl, oxazolyl, isoxazolyl, furazanyl, phenoxazinyl, thieno[2,3-b]furanyl, 2H-furo[3,2-b]pyranyl, benzoxazolyl or morpholinyl radical.

When R is substituted, it preferably carries as substituents one or more substituents chosen from the group constituted by a free, esterified or etherified hydroxy radical in which the ester or ether part contains from 1 to 18 carbon atoms, such, for example, as acetoxy, methoxy, or benzyloxy, the ketone and oxime functions, a linear, branched or cyclic, saturated or unsaturated, alkyl including up to 18 carbon atoms, for example, methyl, ethyl, propyl or isopropyl, ethenyl or ethynyl, halogen atoms such as fluorine, chlorine or bromine, a group $CF_3$, $SCF_3$, $OCF_3$, $NO_2$, $NH_2$ or $C\equiv N$, phenyl, acyl or alkoxycarbonyl containing from 2 to 8 carbon atoms and alkyl-sulphonyl groups containing from 1 to 6 carbon atoms.

More particularly, the subject of the invention is the compounds with the formula (I) in which R represents a possibly substituted phenyl, as well as those in which R' represents a linear, branched or cyclic alkyl, containing from 3 to 12 carbon atoms, such, for example, as n-pentyl, n-hexyl, n-heptyl or n-octyl.

Among the preferred compounds of the invention, there can be cited the compounds of examples 6 and 7.

The compounds of the formula (I) in which R represents unsubstituted phenyl and R' methyl or ethyl are known chemical compounds described, for example, in Chem. Abstr. (1973), 79, 5204K; J.C.S. Chem. Com. 134 (1982); J. Org. Chem. 49, 1149 (1984). However, the literature does not mention any pharmacological property for these compounds. It has just been discovered that the compounds responding to the general formula (I) above offer useful pharmacological properties: they retard the extinction of the conditioned avoidance response, they retard the disappearance of the learned response. They favour attention, vigilance and memorizing.

Therefore, a subject of the invention is the compounds of the formula (I), as medicaments, useful in particular in the treatment of intellectual or nervous asthenias, memory failures, senescence, and mental fatigue.

The subject of the invention, as medicaments, is more particularly the products of examples 6 and 7.

The usual daily dose is invariable according to the affection concerned, the subject treated and the administration route; it can be between 0.6 mg and 40 mg/kg, for example, between 2 and 20 mg/kg in one or more doses for the product of example 1 administered by oral route.

The subject of the present invention is also the pharmaceutical compositions containing as active principle at least one compound with the formula (I).

The pharmaceutical compositions of the invention can be solid or liquid and are presented in the pharmaceutical forms currently used in human medicine, such as, for example, plain or sugar-coated tablets, capsules, granules, suppositories, and injectable preparations; they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, and preservatives.

Also a subject of the invention is a process for the preparation of compounds with the formula (I), characterized in that a compound with the formula (II):

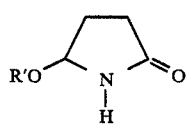

(II)

is submitted to the action of a compound with the formula (III):

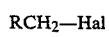 (III)

in which R' retains the same significance as before, and Hal represents a halogen atom, in the presence of a base, in order to obtain the corresponding compound with the formula (I).

In a preferred method of the invention:
Hal represents a bromine atom, the strong base used is an alkali hydroxide such as sodium hydroxide or potassium hydroxide and the operation is done in the presence of a halogenide of tetrabutylammonium, such, for example, as tetrabutylammonium bromide, the condensation of the compounds (II) and (III) takes place in a solvent chosen from the group constituted by tetrahydrofuran, benzene, dimethylformamide, dimethylsulphoxide and diethyl ether of diethylene glycol.

The products with the formula (II) used as starting products are products known in a general way, which can be prepared according to the process described in Tetrahedron 31, 1437 (1975) or Tetrahedron 41, 2007 (1985) or according to the process described in Heterocycles 22, 1733 (1984). Certain preparations of products with the formula (II) are given further on in the examples.

The following examples illustrate the invention without, however, limiting it.

EXAMPLE 1

1-benzyl-2-oxo-5-n-propyloxy-pyrrolidine.

To a mixture of 4 g of 5-(n-propyloxy)-pyrrolidin-2-one, 0.4 g of n-tetrabutylammonium bromide and 2.34 g of potassium hydroxide hydrated to 85% in 70 cm$^3$ of tetrahydrofuran, there is added a solution of 4.78 g of benzyl bromide in 25 cm$^3$ of tetrahydrofuran, operating at between 20° C. and 30° C. After agitating for 1 hour, filtering and then evaporating under reduced pressure, the residue is chromatographed on silica, (eluent: ethyl acetate—n-hexane, 1—1). 4 g of the expected product is obtained.

Analysis: $C_{14}H_{19}NO_2$
Calculated: C % 72.07 H % 8.21 N % 6.00
Found: C % 72.20 H % 8.16 N % 6.22

EXAMPLE 2

1-benzyl-2-oxo-5-isopropoxy pyrrolidine.

To a suspension of 2.5 g of 5-isopropoxy-pyrrolidin-2-one, 1.23 g of potassium hydroxide hydrated to 85%, and 0.25 g of n-tetra-butylammonium bromide in 50 cm$^3$ of tetrahydrofuran, there is added a solution of 2.99 g of benzyl bromide, without exceeding 30° C. After agitating for 1 hour at ambient temperature, the insoluble matter is filtered off and the solvent is evaporated. The residue (4 g) is distilled at 200° C. under 0.05 mbar. The distillate is chromatographed on silica (eluent: ethyl acetate—n-hexane, 1—1). 2.9 g of the expected product is obtained.

Analysis: $C_{14}H_{19}NO_2$
Calculated: C % 72.07 H % 8.21 N % 6.00
Found: C % 71.81 H % 8.06 N % 6.05

EXAMPLE 3

1-benzyl-2-oxo-5-n-butyloxy pyrrolidine.

To a suspension of 4 g of 5-n-butyloxy-pyrrolidin-2-one, 1.79 g of potassium hydroxide hydrated to 85%, and 0.4 g of n-tetrabutylammonium bromide in 80 cm'of tetrahydrofuran, there is added a solution of 4.35 g of benzyl bromide, without exceeding 30° C. After agitating for 1 hour at ambient temperature, the insoluble matter is filtered off and the solvent is evaporated. The residue (4.7 g) is distilled at 230° C. under 0.05 mbar, then the distillate is chromatographed on silica (eluent: ethyl acetate—n-hexane, 1—1). 3.5 g of the expected product is obtained.

Analysis: $C_{15}H_{21}NO_2$
Calculated: C % 72.84 H % 8.56 N % 5.66
Found: C % 72.66 H % 8.65 N % 5.79

EXAMPLE 4

1-benzyl-2-oxo-5-n-pentyloxy pyrrolidine.

To a mixture of 4 g of 5-(n-pentyloxy)-pyrrolidin-2-one, 0.4 g of n-tetrabutylammonium bromide and 1.96 g of potassium hydroxide hydrated to 85% in 60 cm$^3$ of tetrahydrofuran, there is added, without exceeding 30° C. a solution of 3.99 g of benzyl bromide in 20 cm$^3$ of tetrahydrofuran. After agitating for 1 hour at ambient temperature, filtering, evaporating to dryness and chromatographing the residue on silica (eluent: ethyl acetate—n-hexane, 1—1), 4.5 g of the expected product is obtained.

Analysis: $C_{16}H_{23}NO_2$
Calculated: C % 73.53 H % 8.87 N % 5.36
Found: C % 73.71 H % 8.94 N % 5.48

EXAMPLE 5

1-benzyl-2-oxo-5-n-hexyloxy pyrrolidine.

To a mixture of 3.5 g of 5-(n-hexyloxy)-pyrrolidin-2-one, 1.58 g of potassium hydroxide hydrated to 85% and 0.35 g of tetra-n-butylammonium bromide in 50 cm$^3$ of tetrahydrofuran, there is added, at 20° C. to 25° C. a solution of 3.23 g of benzyl bromide in 20 cm$^3$ of tetrahydrofuran. After agitating for 1 hour at ambient temperature, filtering, evaporating to dryness and chromatographing the residue on silica (eluent: ethyl acetate—n-hexane, 1–2), 3.64 g of the expected product is obtained.

Analysis: $C_{17}H_{25}NO_2$
Calculated: C % 74.14 H % 9.15 N % 5.09
Found: C % 74.44 H % 9.25 N % 5.09

EXAMPLE 6

1-benzyl-2-oxo-5-n-heptyloxy pyrrolidine.

To a mixture of 4 g of 5-(n-heptyloxy)-pyrrolidin-2-one, 1.68 g of potassium hydroxide hydrated to 85% and 0.4 g of tetra-n-butylammonium bromide in 55 cm$^3$ of tetrahydrofuran, there is added a solution of 3.43 g of benzyl bromide in 20 cm$^3$ of tetrahydrofuran, operating at 20° C. to 25° C. After agitating for 1 hour at ambient temperature, filtering, and evaporating the solvent to dryness under reduced pressure, the residue is chromatographed on silica (eluent: ethyl acetate—n-hexane, 1–2), and 4.54 g of the expected product is obtained.

Analysis: $C_{18}H_{27}NO_2$
Calculated: C % 74.7 H % 9.40 N % 4.84
Found: C % 74.54 H % 9.36 N % 4.93

EXAMPLE 7

1-benzyl-2-oxo-5-n-octyloxy pyrrolidine.

To a mixture of 2 g of 5-n-octyloxy-pyrrolidin-2-one, 0.65 g of potassium hydroxide at 85% and 0.2 g of tetra-n-butylammonium bromide in 40 cm$^3$ of tetrahydrofuran, there is added a solution of 1.6 g of benzyl bromide in 5 cm$^3$ of tetrahydrofuran, without exceeding 30° C. After agitating for 2 hours at ambient temperature, filtering and evaporating to dryness, the residue is chromatographed on alumina, (eluent: ethyl acetate—cyclohexane, 1—1), and 2 g of the expected product is obtained.

Analysis: $C_{19}H_{29}NO_2$
Calculated: C % 75.20 H % 9.63 N % 4.62
Found: C % 74.98 H % 9.44 N % 4.49

EXAMPLE 8

1-(4-methoxybenzyl)-2-oxo-5-ethoxy-pyrrolidine.

To a mixture of 2.25 g of 5-ethoxy-pyrrolidin-2-one, 1.23 g of hydrated potassium hydroxide and 0.2 g of tetra-n-butylammonium bromide in 45 cm³ of tetrahydrofuran, there is added, without exceeding 30° C., a solution of 3.5 g of 4-methoxybenzyl bromide in 15 cm³ of tetrahydrofuran. After agitating for 1 hour at ambient temperature, filtering and evaporating the solvent under reduced pressure, the residue is taken up with water and extracted with ethyl acetate. The extracts are dried and the solvent is evaporated under reduced pressure. The residue is distilled at 245° C. under 0.2 mbar. 3.10 g of the expected product is obtained.

Analysis: $C_{14}H_{19}NO_3$
Calculated: C % 67.45 H % 7.68 N % 5.62
Found: C % 67.24 H % 7.59 N % 5.66

EXAMPLE 9

1-benzyl-2-oxo-5-n-nonyloxy pyrrolidin-2-one.

To a mixture of 6 g of 5-n-nonyloxy-pyrrolidin-2-one, 1.83 g of potassium hydroxide at 85% and 0.6 g of tetrabutylammonium bromide in 120 cm³ of tetrahydrofuran, there is added, without exceeding 30° C., 4.51 g of benzyl bromide in 9 cm³ of tetrahydrofuran. The mixture is agitated for 2 hours, filtered, then evaporated to dryness. The residue is chromatographed, eluting with a mixture of ethyl acetate and n-hexane (1—1), and 7 g of the expected product is obtained.

Analysis: $C_{20}H_{31}NO_2$
Calculated: C % 75.66 H % 9.84 N % 4.41
Found: C % 75.55 H % 9.87 N % 4.35

EXAMPLE 10

1-benzyl-2-oxo-5-n-decyloxy-pyrrolidin-2-one.

To a mixture of 3 g of 5-n-decyloxy-pyrrolidin-2-one, 0.86 g of potassium hydroxide at 85% and 0.3 g of tetrabutylammonium bromide in 60 cm³ of tetrahydrofuran, there is added, without exceeding 30° C., a solution of 2.12 g of benzyl bromide in 5 cm³ of tetrahydrofuran. The mixture is agitated for 2 hours at ambient temperature, filtered, then evaporated to dryness. The residue is chromatographed on silica (eluent: ethyl acetate—n-hexane, 1—1) and 3 g of the expected product is obtained.

Analysis: $C_{21}H_{33}NO_2$
Calculated: C % 76.09 H % 10.03 N % 4.23
Found: C % 75.88 H % 10.01 N % 4.17

EXAMPLE 11

1-(3-fluoro)-benzyl-2-oxo-5-n-octyloxy-pyrrolidin-2-one.

To a mixture of 2.26 g of 5-n-octyloxy-pyrrolidin-2-one, 0.23 g of tetrabutylammonium bromide and 0.65 g of potassium hydroxide in 40 cm³ of tetrahydrofuran, there is added, without exceeding 30° C., a solution of 2 g of 3-fluorobenzyl bromide in 20 cm³ of tetrahydrofuran. The mixture is agitated for 3 hours at ambient temperature, filtered, and the solvent is evaporated under reduced pressure. The residue is chromatographed on silica (eluent: ethyl acetate—n-hexane, 1—1) and 2.25 g of the expected product is obtained.

Analysis: $C_{19}H_{28}FNO_2$
Calculated: C % 70.99 H % 8.78 N % 4.36
Found: C % 70.68 H % 8.61 N % 4.47

EXAMPLE 12

1-(4-fluoro)-benzyl-2-oxo-5-n-octyloxy-pyrrolidin-2-one.

To a mixture of 2 g of 5-n-octyloxy-pyrrolidin-2-one, 0.2 g of tetrabutylammonium bromide and 0.58 g of potassium hydroxide in 40 cm³ of tetrahydrofuran, there is added, without exceeding 30° C., a solution of 1.77 g of 4-fluorobenzyl bromide in 20 cm³ of tetrahydrofuran. The mixture is agitated for 3 hours at ambient temperature, filtered, and the solvent is evaporated under reduced pressure. The residue is chromatographed on silica (eluent: ethyl acetate—n-hexane, 1—1) and 2.6 g of the expected product is obtained.

Analysis: $C_{19}H_{28}FNO_2$
Calculated: C % 70.99 H % 8.78 N % 4.36
Found: C % 70.75 H % 8.67 N % 4.49

EXAMPLE 13

1-(3-methoxy)-benzyl-5-n-octyloxy-pyrrolidin-2-one

To a mixture of 2.13 g of 5-n-octyloxy-pyrrolidin-2-one, 0.62 g of potassium hydroxide and 0.2 g of tetrabutylammonium bromide in 60 cm³ of tetrahydrofuran, there is added, between 20° C. and 25° C., a solution of 1.57 g of 3-methoxybenzyl chloride in 15 cm³ of tetrahydrofuran. The mixture is agitated for 2 hours at ambient temperature, filtered, and the solvent is evaporated under reduced pressure. The residue is chromatographed on silica (eluent: ethyl acetate—n-hexane, 1—1) and 2.3 g of the expected product is obtained.

Analysis: $C_{20}H_{31}NO_3$
Calculated: C % 72.03 H % 9.37 N % 4.2
Found: C % 71,88 H % 9.46 N % 4.31

EXAMPLE 14

1-(4-methoxy)-benzyl-5-n-octyloxy-pyrrolidin-2-one

To a mixture of 2.13 g of 5-n-octyloxy-pyrrolidin-2-one, 0.62 g of potassium hydroxide and 0.2 g of tetrabutylammonium bromide in 60 cm³ of tetrahydrofuran, there is added, at 20° C./25° C., a solution of 1.57 g of 4-methoxybenzyl bromide in 15 cm³ of tetrahydrofuran. The mixture is agitated for 2 hours at ambient temperature, filtered, and the solvent is evaporated under reduced pressure. The residue is chromatographed on silica (eluent: ethyl acetate—n-hexane, 1—1) and 2.4 g of the expected product is obtained.

Analysis: $C_{20}H_{31}NO_3$
Calculated: C % 72.03 H % 9.37 N % 4.2
Found: C % 71.84 H % 9.26 N % 4.38

EXAMPLE 15

1-(3-trifluoromethyl)benzyl-5-n-octyloxy-pyrrolidin-2-one.

To a mixture of 1.65 g of 5-n-octyloxy-pyrrolidin-2-one, 0.474 g of potassium hydroxide and 0.15 g of tetrabutylammonium bromide in 45 cm³ of tetrahydrofuran, there is added, at 20° C./25° C., a solution of 1.5 g of 3-trifluoromethylbenzyl chloride in 15 cm³ of tetrahydrofuran. The mixture is agitated for 2 hours, filtered, then evaporated to dryness under reduced pressure. The residue is chromatographed on silica (eluent: ethyl acetate—n-hexane, 1—1) and 2.3 g of the expected product is obtained.

Analysis: $C_{20}H_{28}F_3NO_2$
Calculated: C % 64.67 H % 7.60 N % 3.77
Found: C % 64.49 H % 7.48 N % 3.86

EXAMPLE 16

1-(4-trifluoromethyl)benzyl-5-n-octyloxy-pyrrolidin-2-one.

To a mixture of 2.13 g of 5-n-octyloxy-pyrrolidin-2-one, 0.2 g of tetrabutylammonium bromide and 0.62 g of potassium hydroxide in 40 cm$^3$ of tetrahydrofuran, there is added, without exceeding 30° C., 2.39 g of 4-trifluoromethylbenzyl bromide in 40 cm$^3$ of tetrahydrofuran. The mixture is agitated for 3 hours at ambient temperature, filtered, then the solvent is evaporated under reduced pressure. The residue is chromatographed on silica (eluent: ethyl acetate—n-hexane, 1—1) and 2.3 g of the expected product is obtained.

Analysis: $C_{20}H_{28}F_3NO_2$
Calculated: C % 64.67 H % 7.60 N % 3.77
Found: C % 64.45 H % 7.49 N % 3.89

EXAMPLE 17

1-(3-nitro)-benzyl-5-n-octyloxy-pyrrolidin-2-one.

To a mixture of 2.2 g of 5-n-octyloxy-pyrrolidin-2-one, 0.632 g of potassium hydroxide and 0.2 g of tetrabutylammonium bromide in 60 cm$^3$ of tetrahydrofuran, there is added, at 20° C./25° C., 2.2 g of 3-nitrobenzyl bromide in solution in 22 cm$^3$ of tetrahydrofuran. The mixture is agitated for 2 hours at ambient temperature, filtered, then evaporated to dryness under reduced pressure. The residue is chromatographed on silica (eluent: ethyl acetate—n-hexane, 1—1), and 1.6 g of the expected product is obtained.

Analysis: $C_{19}H_{29}N_2O_4$
Calculated: C % 65.49 H % 8.1 N % 8.04
Found: C % 64.93 H % 7.94 N % 7.87

EXAMPLE 18

1-(4-nitro)-benzyl-5-n-octyloxy-pyrrolidin-2-one.

To a mixture of 0.55 g of 5-n-octyloxy-pyrrolidin-2-one, 0.05 g of tetrabutylammonium bromide and 0.16 g of potassium hydroxide in 15 cm$^3$ of tetrahydrofuran, there is added, without exceeding 30° C., a solution of 0.56 g of 4-nitrobenzyl bromide in solution in 10 cm$^3$ of tetrahydrofuran. The mixture is agitated for 30 minutes, then filtered and the solvent is evaporated under reduced pressure. The residue is chromatographed on silica (eluent: ethyl acetate—n-hexane, 1—1), and 0.2 g of the expected product is obtained.

Analysis: $C_{19}H_{28}N_2O_4$
Calculated: C % 65.49 H % 8.1 N % 8.04
Found: C % 65.16 H % 7.92 N % 7.81

EXAMPLE 19

1-(4-phenyl)-benzyl-5-n-octyloxy-pyrrolidin-2-one.

To a mixture of 1.89 g of 5-n-octyloxy-pyrrolidin-2-one, 0.55 g of potassium hydroxide and 0.19 g of tetrabutylammonium bromide in 54 cm$^3$ of tetrahydrofuran, there is added, between 20° C. and 25° C., a solution of 1.8 g of 4-chloromethyldiphenyl in 18 cm$^3$ of tetrahydrofuran. The mixture is agitated for 1 hour at ambient temperature, filtered, and then the solvent is evaporated to dryness. The residue is chromatographed on silica (eluent: ethyl acetate—n-hexane, 1—1), and 1.8 g of the expected product is obtained.

Analysis: $C_{25}H_{33}NO_2$
Calculated: C % 79.11 H % 8.76 N % 3.69
Found: C % 78.88 H % 7.74 N % 3.77

Preparation 1: 5-isopropyloxy pyrrolidin-2-one 28.64 g of succinimide in 1200 cm$^3$ of isopropanol is cooled to −10° C., 32.8 g of hydride of boron and sodium is added, and after keeping for 4 hours at 0°/−10° C., there is added at 0° C./+2° C., while adjusting the pH to 2-3, a 2N solution of hydrochloric acid in isopropanol. After agitating for 2 hours at 0° C., a solution of potassium hydroxide in isopropanol is added until neutral. The solvent is evaporated under reduced pressure, the residue is taken up with chloroform, concentrated to dryness under reduced pressure, and 20.5 g of the expected product is obtained. m.p. 68°-71° C.

Preparation 2

5-n-propyloxy pyrrolidin-2-one.

The operation is done as for preparation 1, using n-propanol with 16 g of sodium borohydride at a temperature between 0°C. and −7° C. 27.5 g of the expected product is obtained. m.p.=52°-54° C.

Preparation 3

5-n-butoxy-pyrrolidin-2-one.

The operation is done as for preparation 2, replacing the isopropanol by n-butanol and employing 14.32 g of succinimide in 600 cm$^3$ of n-butanol and 8 g of boron and sodium hydride. 7.5 g of the expected product is obtained, m.p. 36°-38° C. The product can also be prepared by anodic alkylation according to a process described in Synthesis 4, 315–317 (1980).

Preparation 4

5-pentyloxy-pyrrolidin-2-one.

2.5 g of 5-hydroxy-pyrrolidin-2-one and 1.25 g of Amberlite IR 120H are heated to 65° C. for 3 hours in 55 cm$^3$ of 1-pentanol. The resin is filtered off, and the remainder is distilled under reduced pressure at a temperature of 22° C./24° C. under 0.5 mbar. The residue is chromatographed on silica (eluent: ethyl acetate), and 2.68 g of the expected product is obtained. m.p. 42°-43° C.

Analysis: $C_9H_{17}NO_2$
Calculated: C % 63.13 H % 10.01 N % 8.18
Found: C % 63.31 H % 9.95 N % 8.27

Preparation 5

5-hexyloxy-pyrrolidin-2-one.

A mixture of 0.4 g of 5-hydroxy-pyrrolidin-2-one, 10 cm$^3$ of n-hexanol and 0.2 g of Amberlite IR 120H is heated to 60° C. for 3 hours. The solvent is distilled off at 25° C. under 0.3 mbar. The residue is chromatographed on silica (eluent: ethyl acetate); 0.5 g of the residue is crystallized from hexane, and the expected product is obtained, m.p. 35°-37° C.

Analysis: $C_{10}H_{19}NO_2$
Calculated: C % 64.83 H % 10.34 N % 7.56
Found: C % 64.67 H % 10.25 N % 7.49

Preparation 6

5-n-heptyloxy-pyrrolidin-2-one.

A mixture of 8 g of 5-hydroxy-pyrrolidin-2-one, 100 cm$^3$ of n-heptanol and 4 g of Amberlite IR 120H is heated to 60° C. for 4 hours, filtered, then the solvent is eliminated under 0.3 mbar at 45° C./60° C. 11.9 g of the expected product is obtained, m.p. 52°-54° C., crystallized from hexane.

Analysis: $C_{11}H_{21}NO_2$
Calculated: C % 66.29 H % 10.62 N % 7.03
Found: C % 66.13 H % 10.51 N % 6.98

Preparation 7

5-n-octyloxy-pyrrolidin-2-one.

7.5 g of 5-hydroxy-pyrrolidin-2-one, 10 cm$^3$ of n-octanol and 4 g of Amberlite IR 120H are heated to 60° C. for 4 hours. After filtering, the n-octanol is eliminated by distilling under reduced pressure. 5.5 g of the expected product is obtained, m.p. 36°–38° C., crystallized from hexane.

Analysis: $C_{12}H_{23}NO_2$
Calculated: C % 67.56 H % 10.87 N % 6.57
Found: C % 67.32 H % 10.73 N % 6.69

Preparation 8

5-n-nonyloxy-pyrrolidin-2-one.

A mixture of 5 g of 5-hydroxy-pyrrolidin-2-one 2.5 g of Amberlite IR 120H in 100 cm³ of n-nonanol is agitated at 60° C. for 3 hours. It is then cooled. the resin is filtered off, and the solvent is eliminated by distilling at 70° C. under 0.5 mbar. The residue is taken up in 50 cm³ of n-hexane, which is maintained for 16 hours at 5° C. After separating, 6.8 g of the expected product is obtained, m.p. 46°–48° C. After recrystallizing from n-hexane, m.p. 51°–52° C.

Analysis: $C_{13}H_{25}NO_2$
Calculated: C % 68.68 H % 11.08 N % 6.16
Found: C % 68.33 H % 11.20 N % 6.30

Preparation 9

5-n-decyloxy-pyrrolidin-2-one.

3 g of 5-hydroxy-pyrrolidin-2-one and 1.5 g of Amberlite resin IR 120H in 60 cm³ of n-decanol are agitated at 60° C. for 3 hours. The resin is filtered off and the solvent is eliminated by distilling at 60° C. under 0.4 mm of Hg. The residue is taken up in 50 cm³ of n-hexane, kept for 24 hours at $-5°$ C./$-10°$ C., separated, and 3.5 g of the expected product is obtained, m.p. 44°–46° C. After re-crystallizing from n-hexane, m.p. 48°–49° C.

Analysis: $C_{14}H_{27}NO_2$
Calculated: C % 69.66 H % 11.27 N % 5.80
Found: C % 69.39 H % 11.30 N % 5.84

Examples of pharmaceutical compositions.

(a) Tablets have been prepared of the following formula: Product of example 6: 100 mg Excipient q.s. for a tablet finished at: 300 mg (Detail of excipient: lactose, corn starch, treated starch, rice starch, magnesium stearate, talc).

(b) Capsules have been prepared of the following formula: Product of example 7: 200 mg Excipient q.s. for a tablet finished at: 300 mg (Detail of excipient: talc, magnesium stearate, aerosil).

PHARMACOLOGICAL STUDY

Acute toxicity and behaviour of the invention products.

There were used male mice (Charles Rivers $CD_1$) weighing 22–23 g, without food for 16 hours. The products were administered to them by oral route at doses of 1000–500–250 mg/kg.

The effect of the products on the behaviour of the animals was evaluated according to the method described by Irvin (Psychopharmacologia (1968), 13, 222–257) during the first 8 hours and on the 24th hour.

The mortality was noted during the 7 days following the treatment.

The $LD_{50}$ was thus found to be greater than 1000 mg/kg on the products of examples 1, 3 to 7, 9 and 10.

Learning and Memorizing.

There were used male mice (Charles Rivers $CD_1$) weighing 25–30 g. The animals were placed in the luminous part of a box with two compartments communicating by an opening (G. Galliani, R. Cesana and F. Barzaghi, Med. Sci. Res. 15, 313–314 (1987)).

At the instant when the mouse passes from the luminous compartment to the dark compartment, the opening closes and it is immediately punished by an electric discharge to the paws. The animal submitted to this procedure learns to memorize the punishment. In fact, if it is put back in the luminous compartment, it will thus avoid crossing the opening and re-entering the dark compartment.

In order to induce a retrograde amnesia, the animals are submitted immediately after learning to an electric shock. After the electric shock, the products are administered by oral route at doses of 25; 50; 100; 200 and 400 mg/kg.

We used from 10 to 50 animals per dose.

The anti-amnesic effect of the products is evaluated 3 hours after the treatment, using the same procedure as that utilized for the acquisition.

The time taken by the animal to return to the dark chamber (time limit 180 seconds) is used as evaluation parameter.

In the same experimental conditions, the control animals enter with a time lapse of 40–50 seconds.

The active products are those which cause a significant increase in the latency time.

The results are expressed as percentages of the increase of the latency time in comparison with the corresponding controls. Results obtained with two reference products are provided.

The following Table shows the results:

TABLE

| | Percentage increase in latency time in comparison with the controls | | | | |
|---|---|---|---|---|---|
| | Dose mg/kg per os | | | | |
| Product of example | 400 | 200 | 100 | 50 | 25 |
| 6 | 24 | 99* | 56* | 41 | 16 |
| 7 | — | 68* | 94* | 56 | 33 |
| PIRACETAM | — | 20 | 48* | 10 | 19 |
| AMIRACETAM | — | 32 | 88* | 77 | 39 |

*Values statistically different in comparison with controls.

Conclusion:

The products of examples 6 and 7 are seen to be more active than the controls. They particularly improve the behaviour of the animals in a larger range of doses than in the case of Amiracetam or Piracetam.

What is claimed is:

1. Compounds of the formula (I):

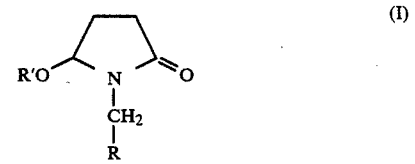

in which R' represents hydrogen, linear, branched or cyclic alkyl containing up to 12 carbon atoms, alkenyl containing from 2 to 8 carbon atoms, acetyl, propionyl, butynyl or aralkyl containing from 7 to 15 carbon atoms and R represents phenyl, possibly substituted by one or more substituents selected from the group consisting of a free, esterified or etherified hydroxy radical in which the ester or ether part contains from 1 to 18 carbon atoms, the ketone and oxime functions, a linear, branched or cyclic, alkyl or alkenyl having up to 18 carbon atoms, halogen atoms, $CF_3$, $SCF_3$, $OCF_3$, $NO_2$, $NH_2$, $C\equiv N$, phenyl, or alkoxycarbonyl containing from 2 to 8 carbon atoms and alkyl-sulphonyl containing from 1 to 6 carbon atoms, provided that if R is unsubstituted phenyl, R' does not represent methyl or ethyl.

2. Compounds of the formula (I) as defined in claim 1, in which R represents a possibly substituted phenyl.

3. Compounds of the formula (I) as defined in claim 1 or 2 in which R' represents a linear, branched or cyclic alkyl containing from 3 to 12 carbon atoms.

4. Compounds of the formula (I) as defined in claim 3, in which R' represents n-pentyl, n-hexyl, n-heptyl or n-octyl.

5. A compound as defined in claim 1, selected from the group consisting of 1-benzyl-2-oxo-5-n-heptyloxy-pyrrolidine, and 1-benzyl-2-oxo-5-n-octyloxy-pyrrolidine.

6. A therapeutic composition comprising a therapeutically effective amount of a compound as defined in any one of claims 1, 2, 4 or 5, and a pharmaceutically acceptable carrier.

7. A therapeutic composition comprising a therapeutically effective amount of a compound as defined in claim 3, and a pharmaceutically acceptable carrier.

* * * * *